United States Patent
Bolskar et al.

(10) Patent No.: US 11,897,983 B2
(45) Date of Patent: Feb. 13, 2024

(54) HYDROLYSIS-TOLERANT CROSSLINKED POLYMERS FROM REVERSE-ACRYLATE MULTIFUNCTIONAL MONOMERS

(71) Applicant: TDA Research, Inc, Wheat Ridge, CO (US)

(72) Inventors: Robert Donald Bolskar, Arvada, CO (US); James William Raebiger, Golden, CO (US); Rhia M Martin, Arvada, CO (US); Silvia De Vito Luebben, Golden, CO (US)

(73) Assignee: TDA Research, Inc., Wheat Ridge, CO (US)

( * ) Notice: Subject to any disclaimer, the term of this patent is extended or adjusted under 35 U.S.C. 154(b) by 164 days.

(21) Appl. No.: 17/203,648

(22) Filed: Mar. 16, 2021

(65) Prior Publication Data
US 2021/0309778 A1 Oct. 7, 2021

Related U.S. Application Data

(60) Provisional application No. 63/000,303, filed on Mar. 26, 2020.

(51) Int. Cl.
*C08F 222/10* (2006.01)

(52) U.S. Cl.
CPC .... *C08F 222/1025* (2020.02); *C08F 2438/00* (2013.01)

(58) Field of Classification Search
CPC .......... C08F 222/1025; C08F 2438/00
See application file for complete search history.

(56) References Cited

U.S. PATENT DOCUMENTS

2020/0197894 A1* 6/2020 Weitz .................. B01F 23/41

FOREIGN PATENT DOCUMENTS

KR 2006-0042362 A * 5/2006 ............. C07C 67/06

* cited by examiner

*Primary Examiner* — Robert D Harlan
(74) *Attorney, Agent, or Firm* — Brian J Elliott; Grace B Clinger

(57) ABSTRACT

Crosslink-forming monomers, comprising reverse-acrylate groups, and crosslinked polymer networks formed by the polymerization of monomers that comprise said reverse-acrylate crosslink-forming monomers. Crosslink-forming monomers, comprising reverse-acrylate groups, comprising an alkyl, an aryl, an alkoxyl, and an alkylamino group bridging one or more reverse-acrylate groups. Crosslink-forming monomers, comprising reverse-acrylate groups, comprising an alkyl, an aryl, an alkoxyl, and an alkylamino ester groups. Crosslink-forming monomers, comprising reverse-acrylate groups, comprising alkyl groups where the group is selected from the group consisting of a methyl, an ethyl, a propyl, an n-butyl and a t-butyl. Reverse-acrylate crosslink-forming monomers comprise a chemical structure where the two or more polymerizable carbon-carbon double bonds are connected by a crosslinking group on the opposite side of the hydrolysable ester groups relative to normal crosslinking acrylate monomers. The crosslink-forming monomers herein form crosslinked polymer networks that do not lose their crosslinking upon hydrolysis of the ester linkages.

11 Claims, 28 Drawing Sheets

1

2

3

4

70

TEGDMA

Bis-GMA

EGEMA reverse acrylate

DMDPEMA reverse acrylate

| Control monomer and initiator mixture | Curing result | Approximate time to cure |
|---|---|---|
| EGDMA + Ph$_2$I$^+$ | no cure with UV or visible | - |
| EGDMA + CQ | no cure with visible | - |
| EGDMA + Ph$_2$I$^+$ + CQ | cures with visible light | 2 min |
| EGDMA + HMPP | cures with UV | 5 min |
| EGDMA + HMPP + CQ | cures with visible light | 2 min |
| | | |
| Monomer and initiator mixture | Curing result | Approximate time to cure |
| EGEMA + HMPP | cures with UV | 5 min |
| EGEMA + HMPP + CQ | cures with visible | 2 min |

Fig. 28

HYDROLYSIS-TOLERANT CROSSLINKED POLYMERS FROM REVERSE-ACRYLATE MULTIFUNCTIONAL MONOMERS

STATEMENT REGARDING FEDERALLY SPONSORED RESEARCH OR DEVELOPMENT

This invention was made using U.S. government funding through the National Institutes of Health, SBIR Phase I Contract No. 1 R43 DE024013-01. The government has certain rights in this invention.

FIELD OF THE INVENTION

The field of the invention relates to crosslinking monomers that form crosslinked polymer networks via a free radical polymerization, an anionic polymerization, a cationic polymerization or other addition polymerization mechanism propagated through carbon-carbon double bonds. The field of the invention also relates to polymer networks made with these crosslinking monomers.

BACKGROUND OF THE INVENTION

Crosslinked polymers made from acrylate monomers, methacrylate monomers, ethacrylate monomers, etc. form polymer networks that contain hydrolysable ester bonds. This leads to ester bond cleavage under hydrolytic conditions, for example being exposed to water, aqueous solutions of an acid, or aqueous solutions of certain enzymes or microbes capable of promoting the hydrolysis. Current crosslinked acrylate or methacrylate-based polymers are susceptible to polymer breakdown upon hydrolysis because the ester bonds (which can hydrolytically or oxidatively cleave) are located internally to the crosslinks that hold together the polymer chains. Thus, hydrolysis reactions eventually cause the polymer chains to no longer be crosslinked, or to reduce the level of crosslinking by cleaving these internal connecting groups.

Examples of crosslinked polymers include mixtures of methacrylate esters such as bis-GMA (bisphenol A di-glycidyl methacrylate) and TEGDMA (triethyleneglycol dimethacrylate). Other methacrylate monomers can be added to impart specific mechanical or chemical properties or to alter specific properties. For example, urethane dimethacrylates may reduce water uptake and polymerization shrinkage, and bis(acrylamide)s may impart improved hydrolytic resistance. However, even with modifications, (meth)acrylate-based polymer networks still have limitations due to their susceptibility to hydrolytic degradation.

Acrylate and methacrylate resins have a degradation rate that is a function of the initial water uptake and is inherent because of the presence of ester bonds in the monomers, which slowly undergo hydrolytic scission. Once started, the degradation accelerates because ester hydrolysis is acid-catalyzed and the hydrolysis product is a carboxylic acid, which lowers the pH in its micro-environment and accelerates the degradation of surrounding ester bonds until mechanical failure occurs. Additionally, the degradation of methacrylate resins may be even faster in the presence of biological agents which may also enzymatically hydrolyze the ester bonds.

Crosslinked (meth)acrylate polymers are used in a wide variety of applications including in adhesives, optical lenses, biomaterials and dental resins and there is need for improved crosslinked polymers that have higher hydrolysis resistance to increase their longevity and reduce the loss of crosslinks due to ester bond cleavage.

BRIEF SUMMARY OF THE INVENTION

The present invention solves the limitation of the prior art by providing a crosslinkable monomer that does not lose crosslinking groups when ester bond hydrolysis occurs. Rather, the monomers of the present invention form crosslinked polymer networks that only lose pendant side chains when hydrolysis occurs, thus crosslinking is not reduced. The present invention provides a monomer that can be polymerized using the same mechanisms as (meth)acrylates, for example by free radical, cationic or anionic polymerization, but that avoids the loss of crosslinks under hydrolytic conditions due to a critical structural difference: in contrast to conventional acrylate or methacrylate monomers, the monomers of the present invention are "reverse acrylates", having the direction of the ester bond "flipped" in relation to the internal crosslinking segment of the monomer. When hydrolysis occurs only the short, pendant alkyl group is lost; for example, by release of a methanol or ethanol molecule, etc. The crosslinking monomers of the present invention can be co-polymerized with other conventional acrylates, methacrylates, etc. because they have similar reactivity under addition polymerization conditions.

The monomers of the present invention most generally have a chemical structure of a diaklyl bis(alkacrylate),

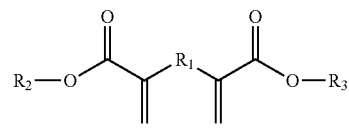

wherein, $R_1$ is selected from the group consisting of an alkyl, an aryl, an alkoxyl, and an alkylamino; wherein, $R_2$ is selected from the group consisting of an alkyl, an aryl, an alkoxyl, and an alkylamino; and $R_3$ is selected from the group consisting of an alkyl, an aryl, an alkoxyl, and an alkylamine, preferably wherein $R_2$ is selected from the group consisting of a methyl, an ethyl, a propyl, an n-butyl and a t-butyl; and wherein, $R_3$ is selected from the group consisting of a methyl, an ethyl, a propyl, an n-butyl and a t-butyl.

In one preferred embodiment, the crosslink-forming monomer has $R_2$ and $R_3$ where they are each an ethyl group, the crosslink-forming monomer comprising the chemical structure:

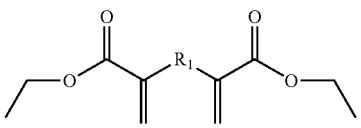

wherein, $R_1$ is selected from the group consisting of an alkyl, an aryl, an alkoxyl, and an alkylamino.

In preferred embodiments, the crosslink-forming monomer further comprising the chemical structure:

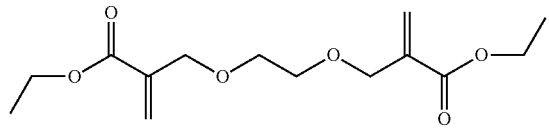

or alternatively the chemical structure:

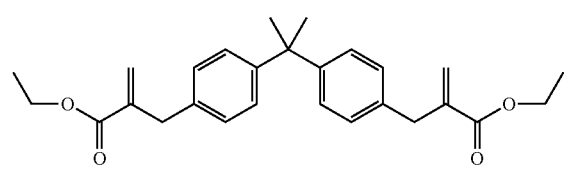

In another embodiment, the present invention provides a crosslinked polymer network comprising crosslinks formed from the polymerization of the previously mentioned crosslink-forming monomers, wherein the crosslinked polymer network comprises a plurality of crosslink group having the chemical structure:

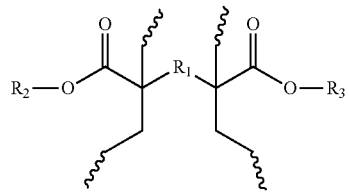

wherein, $R_1$ is selected from the group consisting of an alkyl, an aryl, an alkoxyl, and an alkylamino; wherein, $R_2$ is selected from the group consisting of an alkyl, an aryl, an alkoxyl, and an alkylamino; and $R_3$ is selected from the group consisting of an alkyl, an aryl, an alkoxyl, and an alkylamino.

In preferred embodiments the crosslinked polymer network, comprises a plurality of crosslink group having the chemical structure:

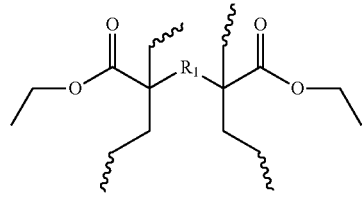

wherein, $R_1$ is selected from the group consisting of an alkyl, an aryl, an alkoxyl, and an alkylamino.

In further preferred embodiments, the crosslinked polymer network of comprises a plurality of crosslink group having the chemical structure:

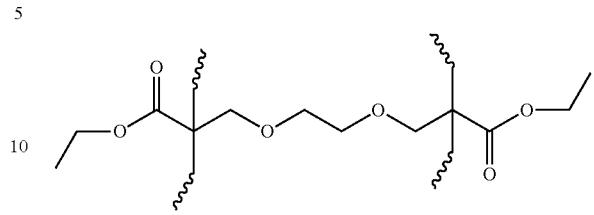

or alternatively the chemical structure:

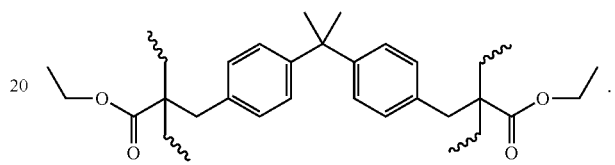

BRIEF DESCRIPTION OF THE DRAWINGS

FIG. 28. Qualitative light-induced curing tests of EGE-reverse-MA in comparison to EGDMA under various different conditions.

DETAILED DESCRIPTION OF THE INVENTION

The present invention provides new materials for making hydrolytically-resistant crosslinked polymer networks. In contrast, current monomers that make up typical non-hydrolysis tolerant methacrylate-based crosslinked polymer networks include ethylene glycol dimethacrylate (EGDMA), triethyleneglycol dimethacrylate (TEGDMA), and bisphenol A di-glycidyl methacrylate (bis-GMA), which have ester bonds that are internal to the subsequently-formed polymer chain. Thus, this type of conventional monomer is susceptible to polymer breakdown upon hydrolysis of these ester linkages. The present invention provides monomer that produce crosslinked polymer networks with similar mechanical properties as conventional methacrylates, and they also can be polymerized using similar reaction mechanisms, such as light- or heat-initiated free radical polymerization, or alternatively anionic or cationic polymerization. Other polymerization mechanisms that are known for C=C bond polymerization are also possible, including thiol-based reactions, sometimes referred to as "living polymerization" or "mediated polymerization". However, the crosslink-forming monomer of the present invention solves the problem of crosslink group loss by hydrolysis.

The crosslinking monomers of the present invention have at least two "reverse acrylate" functional groups connected via a bridging group, the bridging group forming a chemical crosslinking segment once the crosslinking monomers are used to form a polymerized polymer network. Monomers that have two or more functional groups can form crosslinks in polymer networks that are formed by addition mechanisms such as free radical, cationic, anionic polymerization.

Figure 11:
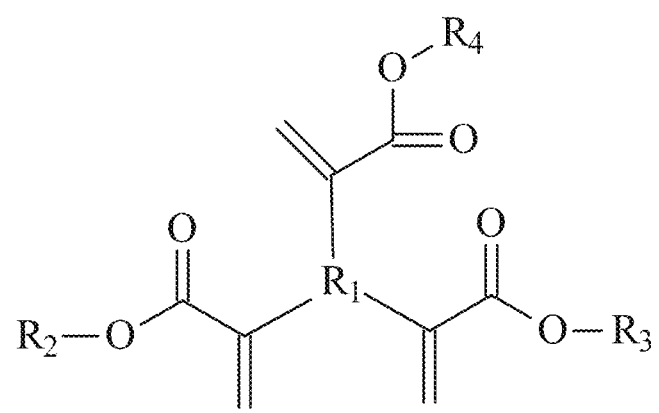
FIG. 11. General chemical structure of a tri-functional reverse-acrylate crosslinking monomer.
Figure 12:
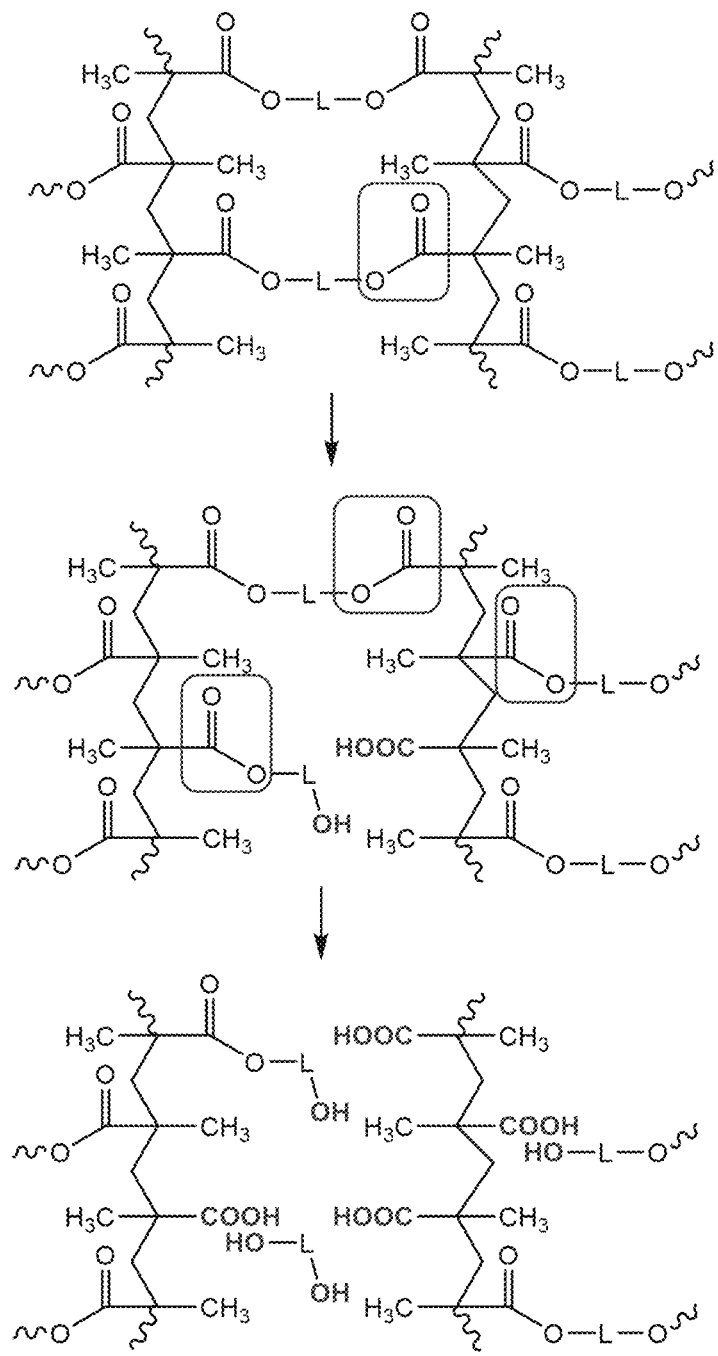
FIG. 12. Illustration of hydrolysable bonds in conventional crosslinked methacrylate polymer network.

Conventional acrylate and methacrylate crosslinking monomers suffer the drawback in that their ester bonds, indicated by the red boxes in FIG. 11, are subject to hydrolysis. When hydrolysis occurs in a crosslinked polymer, the "bridges" that form the crosslinks and that hold the polymeric network together break down and the material disintegrates. This is illustrated in FIG. 11, wherein "L" represents a generic linking group. It is this L group that covalently links the polymer chains to one another, and maintains the polymers' physical and mechanical properties.

However, the presence of the ester bond next to the carbon-carbon double bond (as in the conventional methacrylate monomer) is its key to curing of these monomers, and their high conversion to polymer at room temperature and the low incidence of undesired side reaction(s). The present invention provides a unique solution to the problem of needing highly reactive monomers but the need to avoid the loss of crosslinks by hydrolysis by "flipping" the structure of the molecule as illustrated in the structural comparisons shown in FIG. 5 vs. FIG. 6. In the Specification and in the accompanying Listing of Claims and in the Drawings, this reversed or flipped functional group structure is called a "reverse acrylate", or alternatively the symmetrical (di-functional) crosslinking monomer is generically called a bis(alkacrylate). When hydrolysis occurs only the short, pendant alkyl group is lost. For example, a methanol or an ethanol molecule is released.

Figure 3:
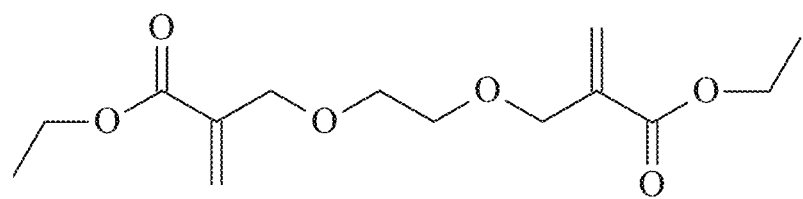
FIG. 3. Chemical structure of diethyl bis(dimethoxyethyleneglycol-alkacylate), also referred to herein as ethylene glycol ethyl-reverse-methacrylate (EGE-reverse-MA).
Figure 4:
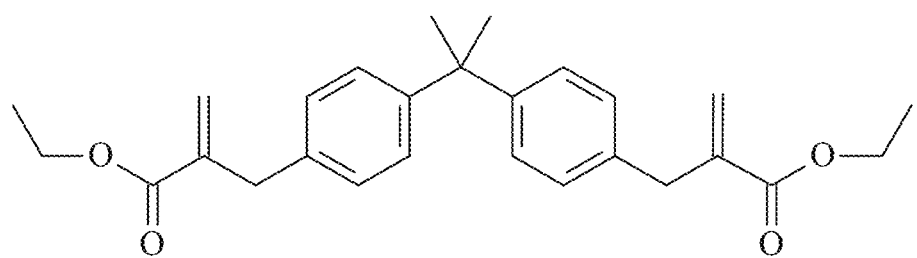
FIG. 4. Chemical structure of diethyl bis(dimethyldiphenylmethane-alkacrylate), also referred to herein as dimethyldiphenylmethane ethyl-reverse-methacrylate (DMDPE-reverse-MA).

Two examples of the crosslinking monomers of the present invention are diethyl bis(dimethoxyethyleneglycol-alkacylate), also referred to herein as ethylene glycol ethyl-"reverse"-methacrylate (EGE-reverse-MA) (see FIG. 3) and diethyl bis(dimethyldiphenylmethane-alkacrylate), also referred to herein as dimethyldiphenylmethane ethyl-"reverse"-methacrylate (DMDPE-reverse-MA) (see FIG. 4). In these example molecules, the "bridge" between the two "reverse"-methacrylate groups does not contain the hydrolysable bonds; the hydrolysable ester groups are simply side chains. Thus, if polymeric materials made from these compounds hydrolyze they would release a small amount of ethanol (or other alcohol), but the crosslinked network would not break down.

Figure 13:
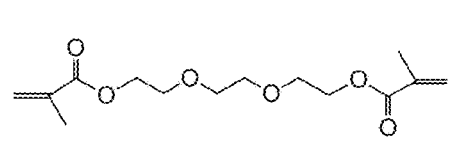
FIG. 13. Comparison of the chemical structure of standard methacrylates and reverse-acrylates with related bridging groups.
Figure 13:
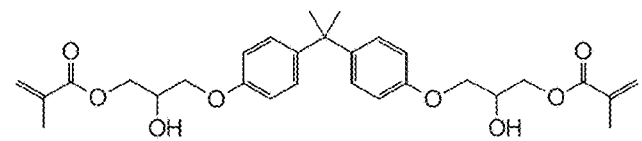
Figure 13:
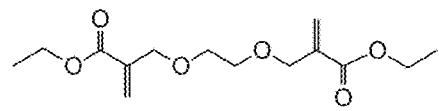
Figure 13:
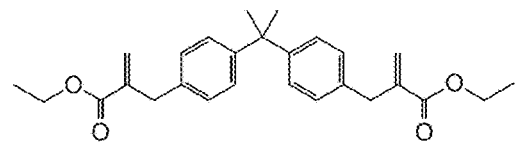
Figure 14:
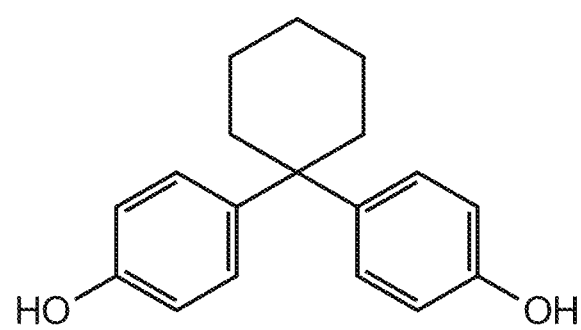
FIG. 14. Chemical structure of p-[1-(p-Hydroxyphenyl)cyclohexyl]phenol (Bisphenol-Z).
Figure 15:
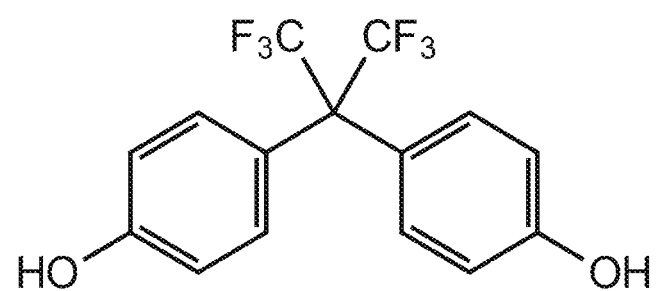
FIG. 15. Chemical structure of p-[2,2,2-Trifluoro-1-(p-hydroxyphenyl)-1-(trifluoromethyl)ethyl]phenol (Bisphenol AF).
Figure 16:
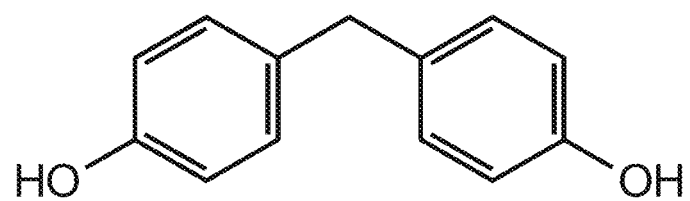
FIG. 16. Chemical structure of p-[(p-Hydroxyphenyl)methyl]phenol (Bisphenol-F).
Figure 17:
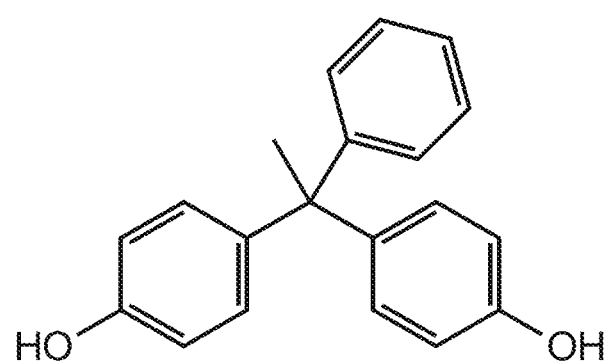
FIG. 17. Chemical structure of p-[1-(p-Hydroxyphenyl)-1-phenylethyl]phenol (Bisphenol-AP).
Figure 18:
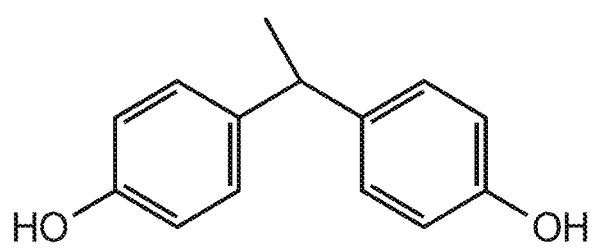
FIG. 18. Chemical structure of p-[1-(p-Hydroxyphenyl) ethyl]phenol (Bisphenol-E).
Figure 19:
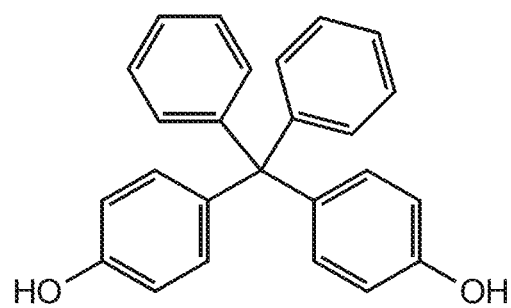
FIG. 19. Chemical structure of p-[(p Hydroxyphenyl) diphenylmethyl] phenol (Bisphenol-BP).
Figure 20:
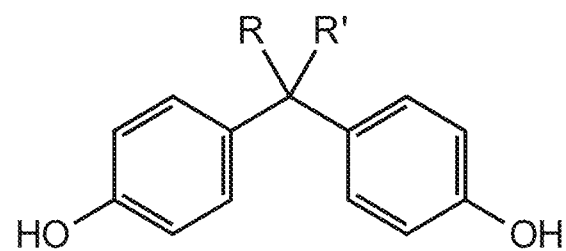
FIG. 20. Chemical structure of a general bisphenol derivative.

FIG. 13 shows a comparison of the conventional monomers TEGDMA and Bis-GMA (upper row), which have hydrolysable esters groups that are internal to the polymer formed upon polymerizing the acrylate groups, to the new reverse-acrylate monomers that the present invention teaches, EGE-reverse-MA and DMDPE-reverse-MA (lower row), which have their esters groups located outside the polymer chain that is formed upon polymerization of the acrylate groups.

In the Specification and the accompanying Listing of Claims, the terms below are given the following meanings.

The term crosslink means a covalently bonded groups that connects two or more polymer chains. The term crosslink is understood by a Person Having Ordinary Skill In The Art.

The term "crosslink-forming monomer" means a monomer that is capable of being chemically reacted in a polymerization reaction to form crosslinks in the resulting polymer network. The term shall not be interpreted to require that the monomer be polymerized or exist in a post-polymer network, rather is capable of being reacted and formed into a crosslink within a polymer network. This latent property is understood by a Person Having Ordinary Skill In The Art. In the Specification and accompanying Listing of Claims of the present application, the term "crosslink-forming monomer" is to be interpreted as interchangeable with the phrase a "monomer to form crosslinks in a polymer network".

The terms "alkyl", aryl", "alkoxyl" and "alkylamino" are to be given their broadest meaning understood by a Person Having Ordinary Skill In The Art.

Figure 1:
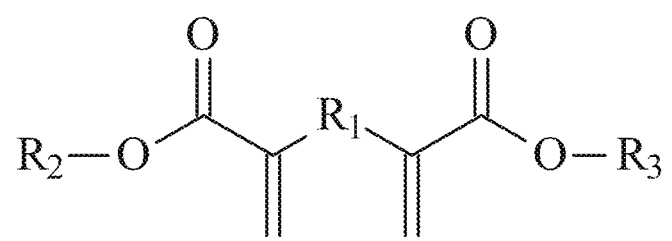
FIG. 1. General chemical structure of a dialkyl bis(alkacrylate) monomer.

The term "dialkyl bis(alkacrylate)" is to be given the broadest chemical structure as defined by FIG. 1.

Figure 5:
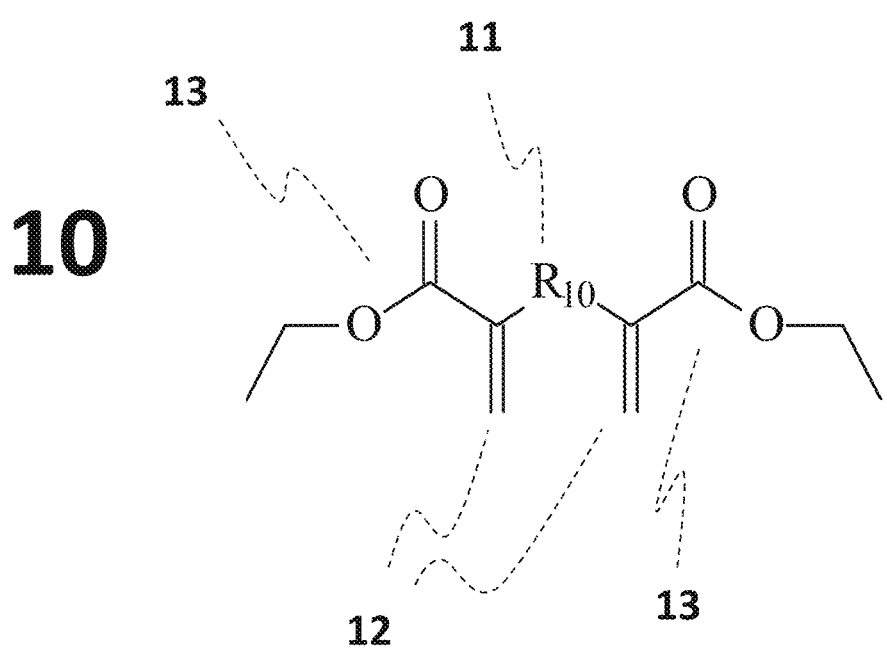
FIG. 5. Structure and features of a "reverse acrylate" crosslinking monomer.

The term "alkacrylate" is to be given the meaning of having the "reverse-acrylate" structure taught by the present invention, as represented in FIG. 5. FIG. 5 illustrates a crosslinking di-alkacrylate, but the term should be interpreted as being applicable to mono-alkacrylates, tri-alkacrylates and muilt-alkacrylates.

The term "reverse-acrylate" is given the meaning described in further detail within the Specification and accompanying Drawings, and has an ester bond-activated C=C double bond, wherein the ester bond is located near the external ends of the monomer, such that the C=C double bond is located internal from the ester bonds and adjacent to the bridging group. The bridging group is the portion of the monomer that becomes the crosslink in a polymer network.

Non-limiting examples of the dialkyl bis(alkacrylate) of the present invention include: diethyl bis(dimethyldiphenylmethacrylate), diethyl bis(alkacrylate), bis(alkylacrylates) and bis(arylacrylates).

FIG. 1 illustrates the general chemical structure 1 for dialkyl bis(alkacrylate). The R1 group will become the crosslink in a polymer network.

Figure 2:
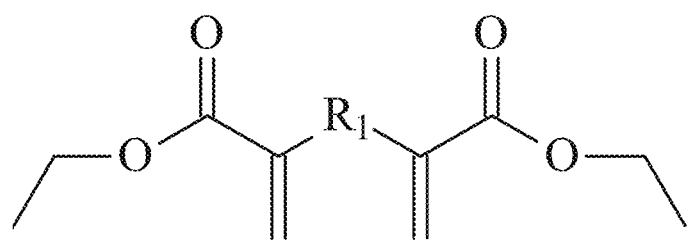
FIG. 2. Chemical structure of diethyl bis(alkacrylate) monomer.

FIG. 2 illustrates the general chemical structure 2 for dialkyl bis(alkacrylate).

FIG. 3 illustrates the structure 3 of a dialkyl bis(alkacrylate), which has ethyl leaving groups and a dimethoxy ethylene glycol crosslink, or bridging, group. The compound is ethylene glycol ethyl-"reverse"-methacrylate) EGE-reverse-MA)).

FIG. 4 illustrates another structure 4 of a dialkyl bis(alkacrylate), which has ethyl leaving groups and an aryl crosslink, or bridging, group. The compound is dimethyldiphenylmethane ethyl-"reverse"-methacrylate (DMDPE-reverse-MA).

The features of a "reverse-acrylate" 10 are illustrated in FIG. 5. Crosslinking monomers that are reverse-acrylates contain a linking group (also referred to as a bridging group) 11, C=C groups 12 that are located adjacent to the linking group 11, and ester bonds 13 located on outer portions of the molecule, further from the linking group 11 than the C=C group 12. The C=C group is located between a linking group 11 and an ester group 13.

Figure 6:
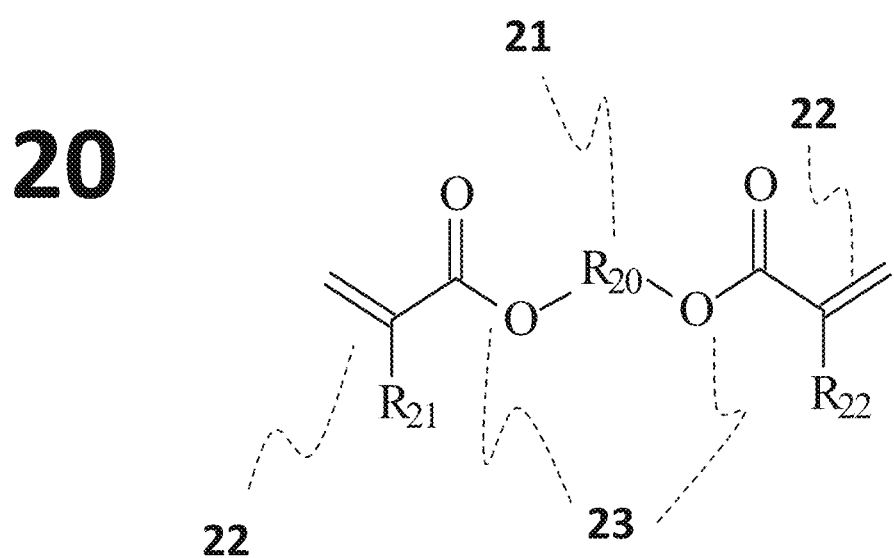
FIG. 6. Structure and features of a standard acrylate crosslinking monomer.

The features of a conventional acrylate (also referred to as a standard acrylate) 20 are illustrated in FIG. 6. Crosslinking monomers that are conventional acrylates contain a linking group (also referred to as a bridging group) 21, ester groups 23 that are located adjacent to the linking group 21, and C=C groups 22 located on outer portions of the molecule, further from the linking group 11 than the ester group 23. The ester group 23 is located between a linking group 21 and a C=C group 22.

Figure 7:
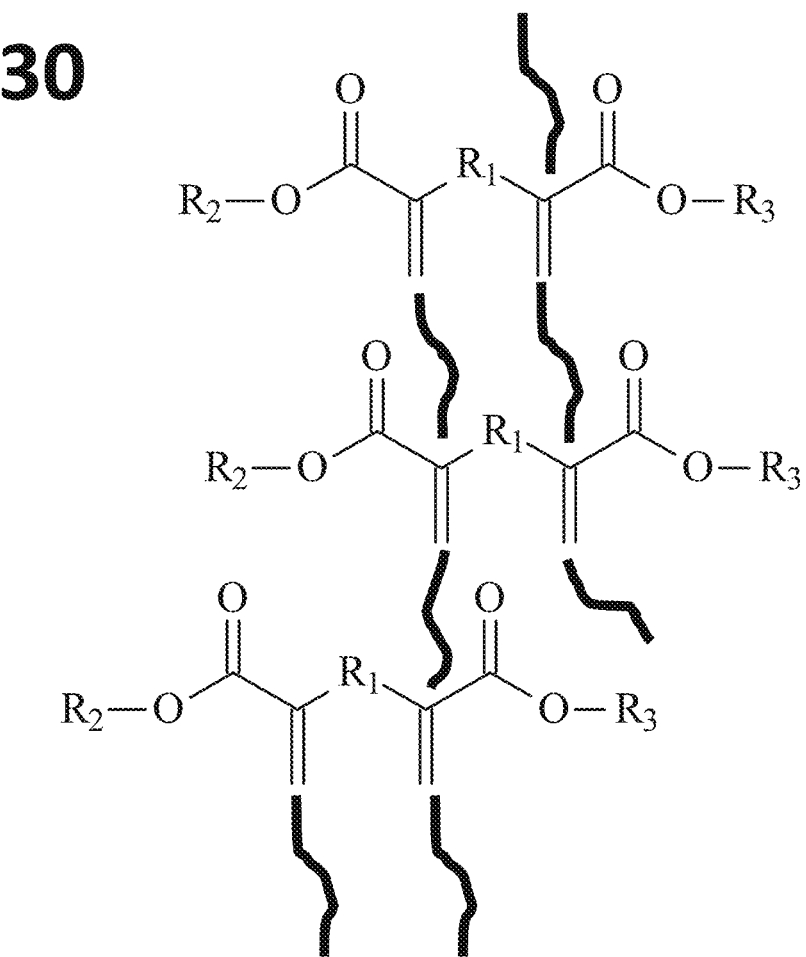
FIG. 7. Crosslinked polymer network formed from the reverse-acrylate crosslinking monomers.
Figure 8:
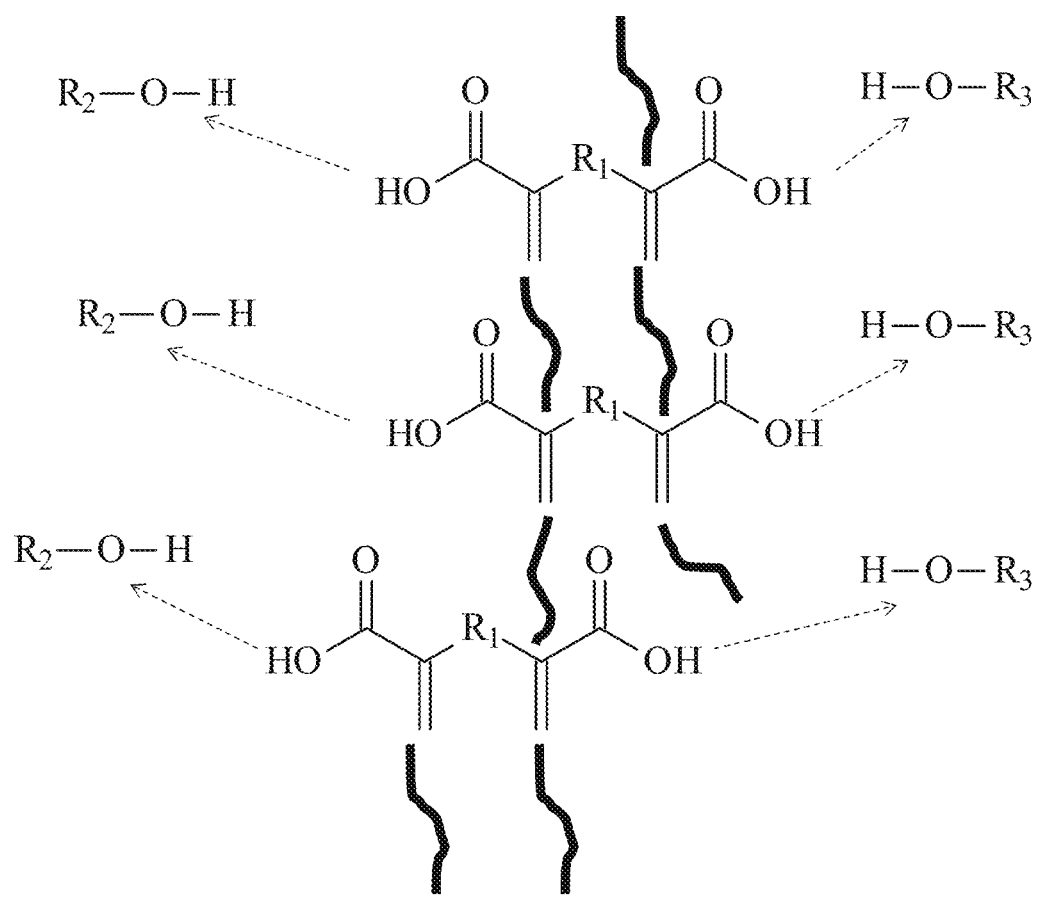
FIG. 8. Crosslinked polymer network formed from the reverse-acrylate crosslinking monomers (post hydrolysis).

A crosslinked polymer network comprising the dialkyl bis(alkacrylate) crosslink-forming monomers 30 is shown in FIG. 7. In the illustration 30, the darker, curved lines represent a generic polymer chain, which can (for example) be formed by a free radical polymerization propagating through the C=C bonds (see FIG. 5, label 12). In FIG. 8, the same crosslinked polymer network is represented now for the post-hydrolysis state, where the pendant $R_2$ and $R_3$ groups have been separated from the crosslinked portion of the polymer network 40.

Figure 9:
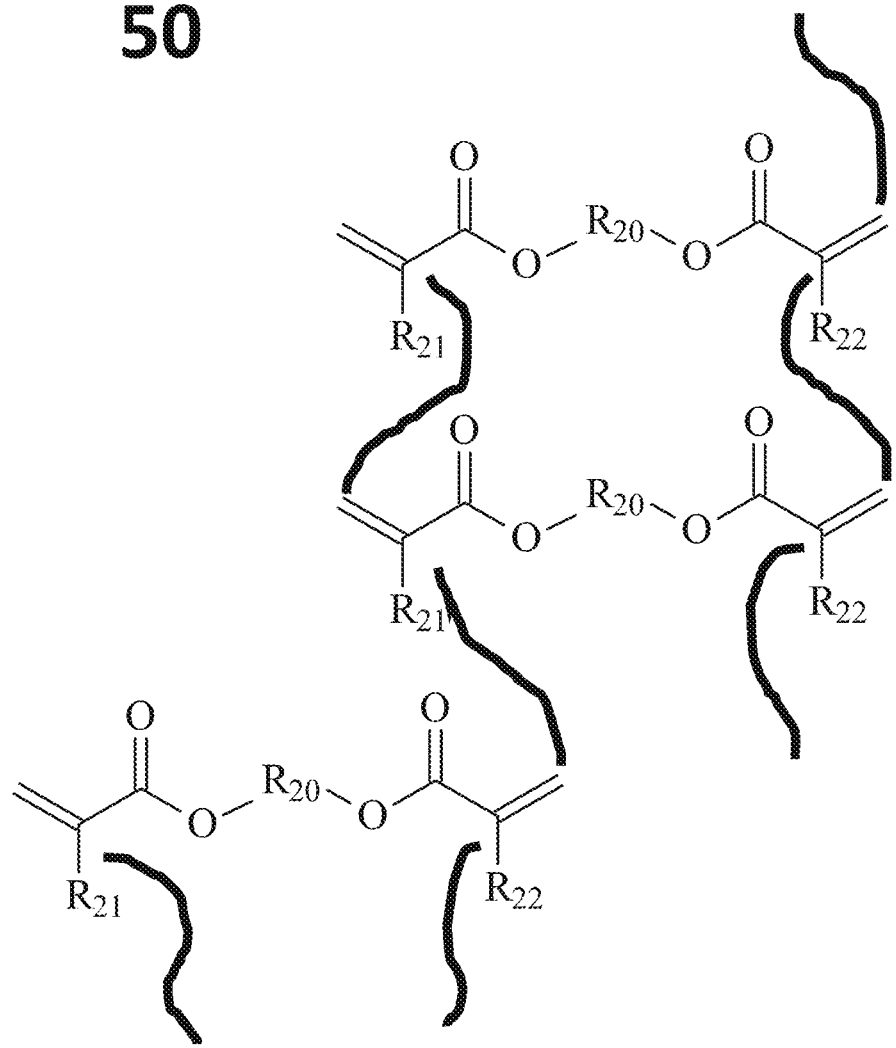
FIG. 9. Crosslinked polymer network formed from standard/conventional acrylate crosslinking monomers.
Figure 10:
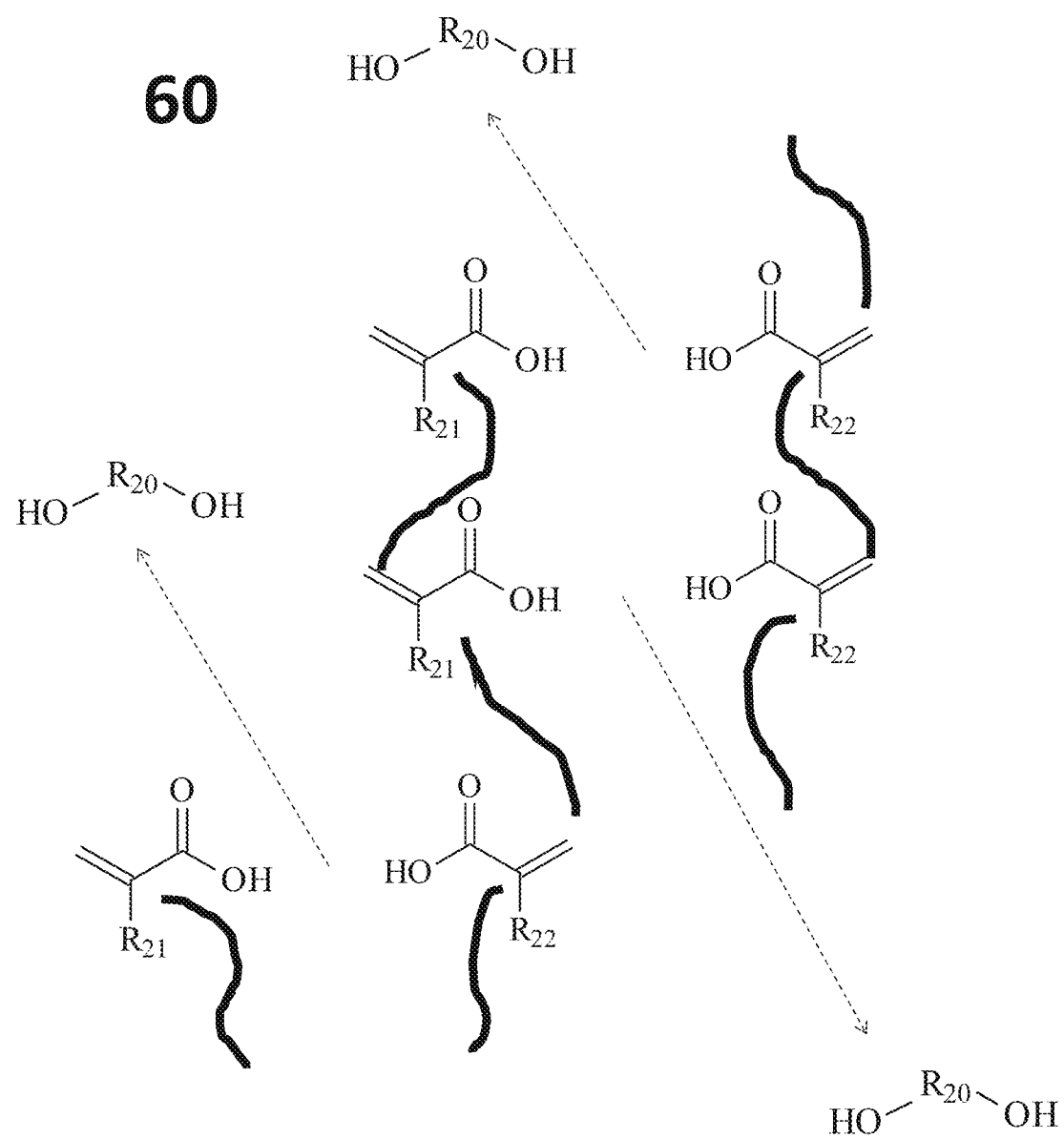
FIG. 10. Crosslinked polymer network formed from standard/conventional acrylate crosslinking monomers (post hydrolysis), now with loss of crosslinks.

A crosslinked polymer network comprising conventional acrylate crosslink-forming monomers 50 is shown in FIG. 9. In the illustration 50, the darker, curved lines represent a generic polymer chain, which can (for example) be formed by a free radical polymerization propagating through the C=C bonds (see FIG. 6, label 22). In FIG. 9, the same crosslinked polymer network is represented now for the post-hydrolysis state, where the internal $R_{20}$ linker groups (also have been separated from the crosslinked portion of the polymer network 40.

Non-limiting examples of aryl groups that can be used as the linking group ($R_1$) are shown in FIG. 14-FIG. 20.

Figure 21:
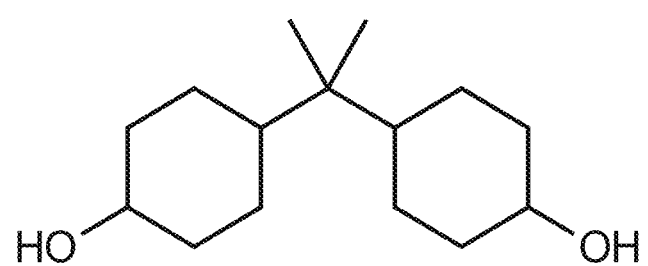
FIG. 21. Chemical structure of 4-[1-(4-Hydroxycyclohexyl)-1 methylethyl]cyclohexanol 4,4'-lsopropylidenedicyclohexanol, mixture of isomers.

A non-limiting example of an alkyl group that can be used as the linking group ($R_1$) is shown in FIG. 21.

In the following examples certain embodiments are described in greater detail. Detailed syntheses and characterization for two monomers are described for ethylene glycol ethyl reverse-methacrylate (EGE-reverse-MA) and dimethyldiphenylmethane ethyl reverse-methacrylate (DMDPE-reverse-MA).

In the examples, precursor chemicals and solvents were obtained from commercial sources and used as received. In certain cases, anaerobic conditions were employed either in an inert-atmosphere glovebox or by using argon with a Schlenk line.

Example 1a: Synthesis of EGE-reverse-MA. Ethylene glycol ethyl reverse-methacrylate (EGE-reverse-MA) can be synthesized according to Scheme 1. This reaction sequence is conducted as a one-pot reaction in which the intermediates are not isolated. The sequence begins with commercially available 1,2-bis(2-iodoethoxy)ethane, which is metallated with zinc and then copper using organometallic transformations like those reported by Knochel and co-workers (Majid 1990; Rao 1990), which are incorporated herein by reference. The metallated intermediates are not isolated; the Cu—Zn transmetallated intermediate is reacted in situ with two equivalents of the electrophile ethyl 2-bromomethylacrylate (commercially available) to generate EGE-reverse-MA.

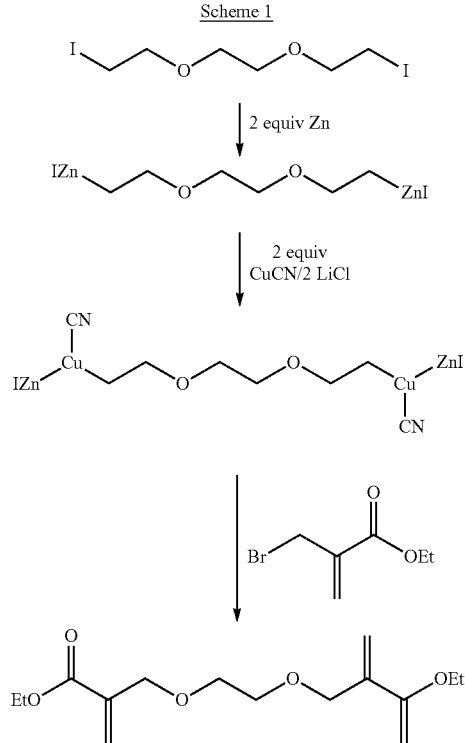

Figure 22:
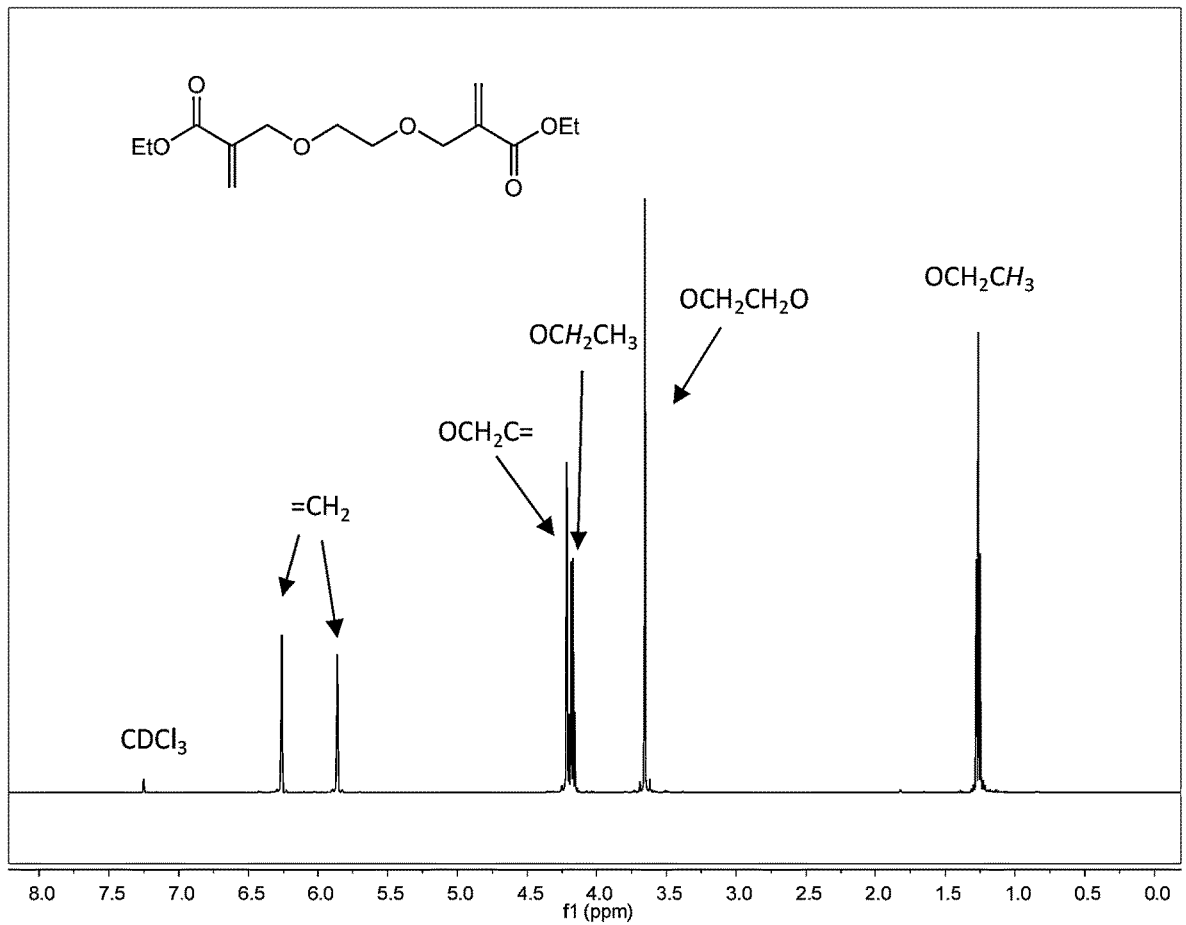
FIG. 22. The $^1$H-NMR spectrum of ethylene glycol ethyl reverse-methacrylate (EGE-reverse-MA).

Example 1 b: Synthesis of the bis-acrylate with ethylene glycol backbone, EGE-reverse-MA. The EGE-reverse-MA monomer was prepared according to the sequence shown in Scheme 1. This preparation was performed under argon. Zn dust (2.16 g, 33.0 mmol) and LiCl (1.40 g, 33.0 mmol) were stirred in 25 mL of anhydrous THF in a 100 mL round bottom flask that was sealed with a septum. Neat 1,2-bis(2-iodoethoxy)ethane (2.00 mL, 11.1 mmol) was added via a syringe and the reaction mixture was refluxed under argon. For the first 30 min, the reaction vigorously bubbled; reflux was continued for a total of 2 hours. After cooling and settling, the cloudy supernatant was transferred to two 15 mL centrifuge tubes. The solutions were centrifuged for 1 hour at 4000 RPM. During this time 1.97 g of CuCN (22.0 mmol) and 1.87 g of LiCl (44.1 mmol) were stirred in 20 mL of anhydrous THF forming a pale-green solution. To this stirred solution was added the clear Zn solution via a syringe causing the reaction solution to immediately become colorless. After 5 min, neat ethyl 2-bromomethylacrylate (3.00 mL, 21.8 mmol, synthesized as described above in Sections E.2.2 and E.2.3) was added via a syringe causing the reaction solution to immediately turn pale yellow. The solution was stirred at ambient temperature overnight resulting in a color change to darker yellow. The reaction was quenched by the addition of 40 mL of saturated aqueous $NH_4Cl$ solution. It was extracted with 3×50 mL of EtOAc. The organic solution was washed with 4×50 mL of $H_2O$ (resulting in the precipitation of a grey, gooey material in the aqueous washings). The solution was washed with 50 mL of brine, dried over $MgSO_4$, filtered, and rotary evaporated. The viscous, yellow crude product was purified by flash chromatography on silica gel eluting with 6:1 hexane:EtOAc. Yield=1.69 g (54%) of a colorless, viscous liquid. $^1$H NMR (CDCl$_3$): 6.28 (s, =CH$_2$, 2H), 5.87 (s, =CH$_2$, 2H), 4.23 (s, OCH$_2$C=, 4H), 4.19 (q, OCH$_2$CH$_3$, 4H), 3.67 (s, OCH$_2$CH$_2$O, 4H), 1.26 (t, OCH$_2$CH$_3$, 6H). MS: m/z 285. The NMR spectrum is shown in FIG. 22.

Example 1c: Synthesis of EGE-reverse-MA. Ethylene glycol ethyl reverse-methacrylate (EGE-reverse-MA) can also be synthesized according to Scheme 2, starting with ethylene glycol as an alternative to the preceding method. In this method, ethylene glycol is first deprotonated using a strong base followed by subsequent reaction with 2-bromomethylacrylate, similar to the reaction of aliphatic alcohols with 2-bromomethylacrylate (Chemla, 2011), which is incorporated herein by reference. This sodium iodide mediated process uses a mild base in air at elevated temperatures.

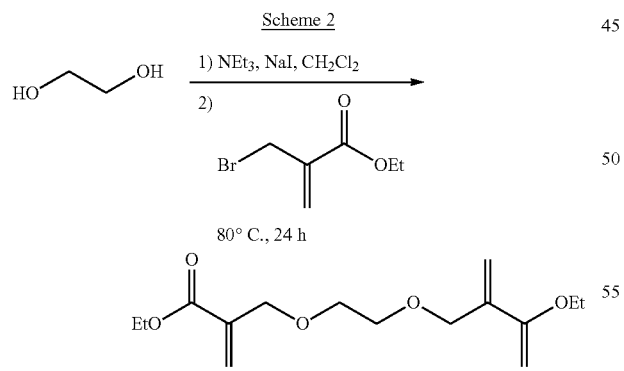

Scheme 2

Example 1d: Alternate synthesis of the bis-acrylate with ethylene glycol backbone, EGE-reverse-MA. 2-Bromomethylacrylate (6.22 g, 32.2 mmol, 4 equiv) was dissolved in DCM (10 mL) in a 100 mL Schlenk tube equipped with stir bar. The tube was chilled in an ice bath. Triethylamine (6.8 mL, 48.3 mmol, 6 equiv) and ethylene glycol (0.45 mL, 8.06 mmol) were added successively, dropwise. Next, sodium iodide (1.33 g, 8.86 mmol, 1.1 equiv) was added. After 10 minutes, the ice bath was removed and the reaction mixture allowed to warm to ambient temperature. The tube was sealed with a Teflon screw top and the reaction mixture heated to 80° C. for 24 hours. The reaction mixture was allowed to cool to ambient temperature and added to a mixture of dichloromethane and 1.2 M HCl (75 mL each). The resulting layers were separated and the aqueous layer extracted with dichloromethane (2×75 mL). The organic layers were combined and washed with brine (2×75 mL). The organic layer was dried over $MgSO_4$ and the solvent removed in vacuo. The resulting yellow oil was purified by column chromatography (5:1 hexanes:EtOAc). Yield=1.6 g (69%) of a pale yellow oil (1.6 g, 69%). $^1$H NMR (CDCl$_3$): δ 6.30 (s, 2H), 5.90 (s, 2H), 4.24 (m, 8H), 3.69 (s, 4H), 1.29 (t, 6H).

Example 2a: Synthesis of DMDPE-reverse-MA. The compound DMDPE-reverse-MA was prepared in three steps using bisphenol-A as a starting material, using the overall reaction sequence shown in Scheme 3.

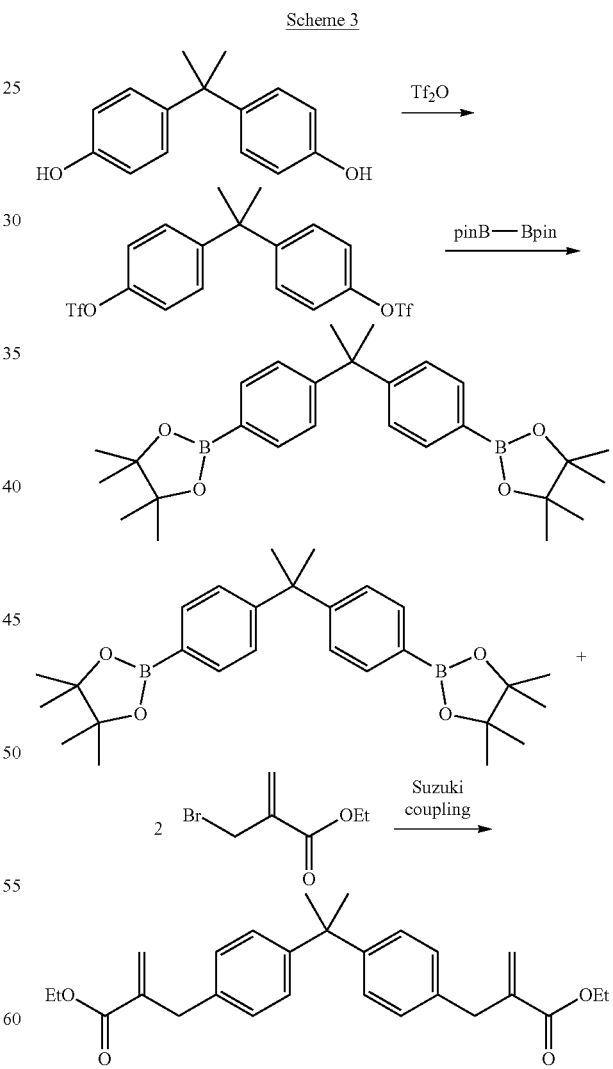

Scheme 3

In the first step, bisphenol-A is converted to the bis-triflate analogue. Then, the triflate groups are substituted by boron bis-pinacolate (Bpin) groups. In the final step, Suzuki coupling is used to couple ethyl-2-bromomethylacylate to the dimethyldiphenylmethane unit of the (Bpin)$_2$ derivative. In the Suzuki coupling, a new carbon-carbon single bond is formed by coupling an organoboron derivative with an alkyl or aryl halide using a ligated Pd catalyst in the presence of base (Miyaura, 1995; Barder, 2005).

Example 1 b: Synthesis of BPA(OTf)$_2$. This reaction was conducted with anhydrous conditions under argon according to Scheme 4.

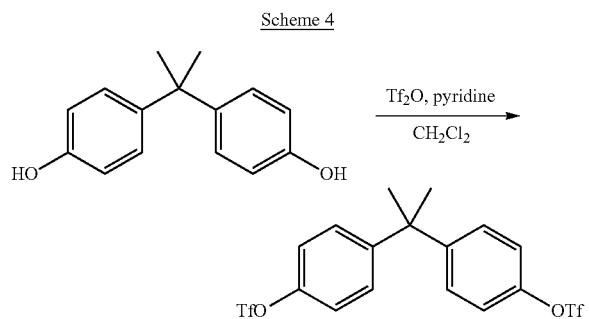

Scheme 4

Figure 23:
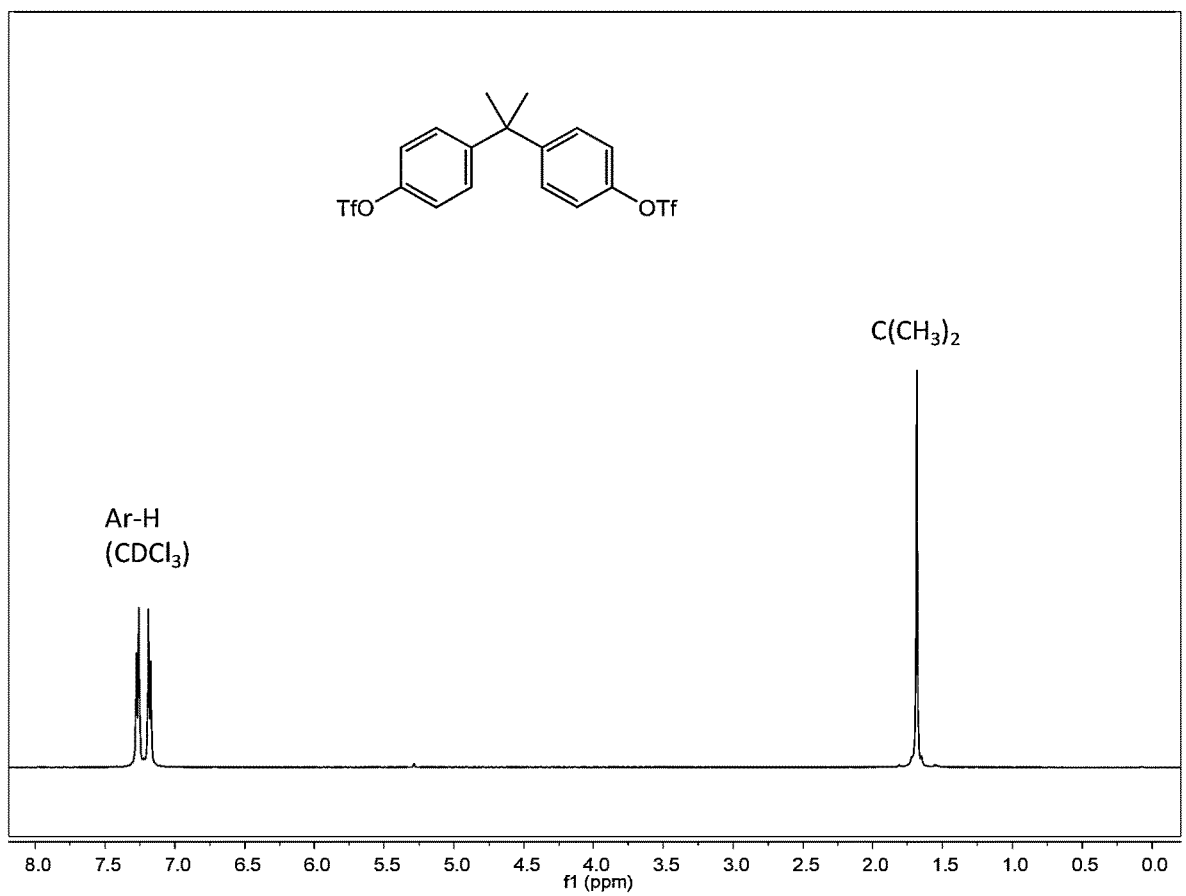
FIG. 23. The $^1$H-NMR spectrum of BPA(OTf)$_2$.

Bisphenol A (2.28 g, 10.0 mmol) was stirred in 40 mL of anhydrous CH$_2$Cl$_2$ in a 100 mL round bottom flask. Pyridine (2.4 mL, 30 mmol) was added via a syringe causing the bisphenol A to dissolve. After cooling in an ice bath, triflic anhydride (4.0 mL, 24 mmol) was added via a syringe. The reaction was stirred at 0° C. for 10 min then at ambient temperature for 1 hour. The reaction was quenched by the addition of 20 mL of 1 M HCl. The organic layer was removed and the aqueous was extracted with 2×20 mL of CH$_2$Cl$_2$. The combined organics were washed with 2×50 mL of H$_2$O followed by 50 mL of brine. The solution was dried over MgSO$_4$, filtered, and rotary evaporated. The product was dried under dynamic vacuum overnight. TLC (4:1 hexane:EtOAc) shows clean conversion from the phenol (R$_f$=0.13) to the aryl triflate (R$_f$=0.65). Yield=4.62 g (92%) of a tan solid. $^1$H NMR (CDCl$_3$): 7.27 (d, Ar—H, 4H), 7.17 (d, Ar—H, 4H), 1.68 (s, CH$_3$, 6H). The NMR spectrum is shown in FIG. 23.

Example 2c: Synthesis of dimethyldiphenylmethane(Bpin)$_2$, according to Scheme 5.

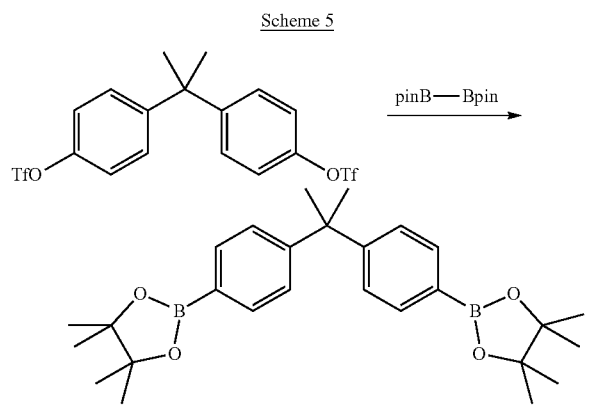

Scheme 5

Figure 24:
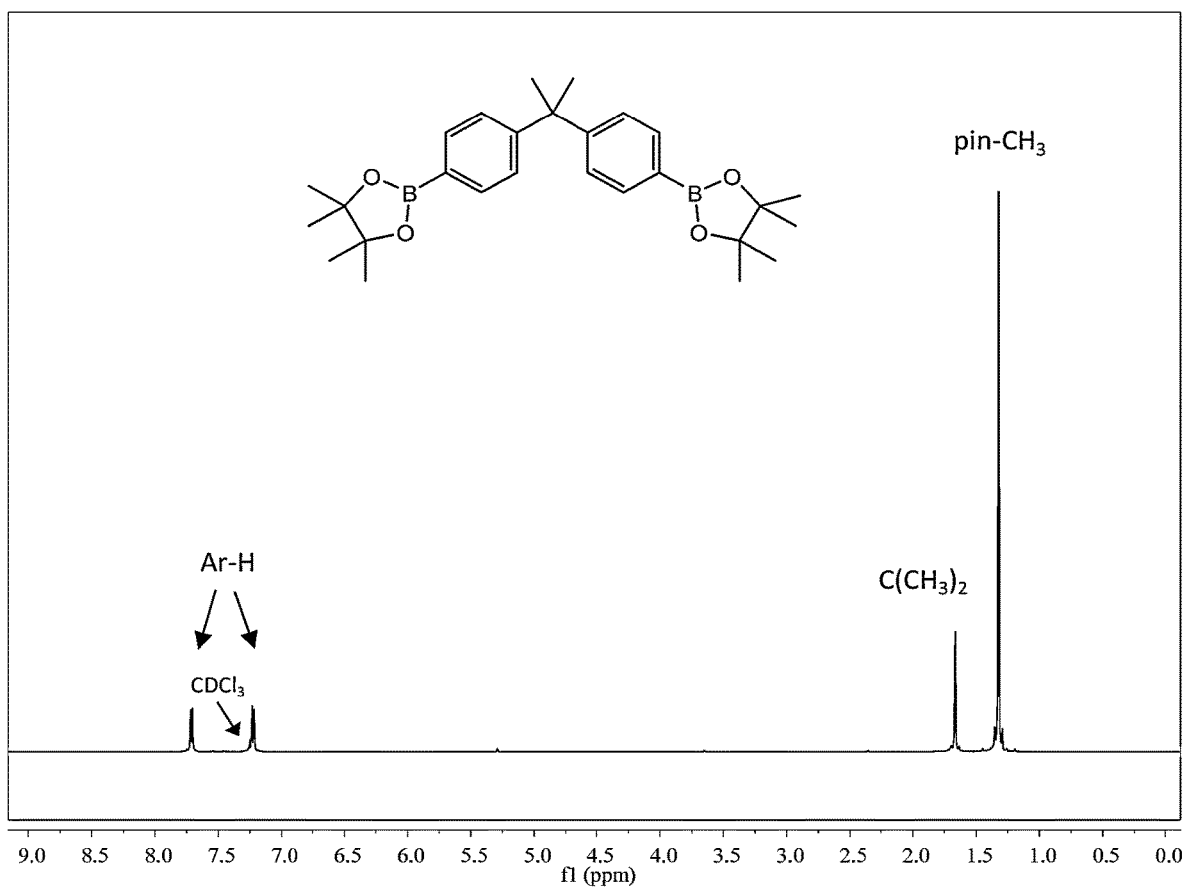
FIG. 24. The $^1$H-NMR spectrum of dimethyldiphenylmethane(Bpin)$_2$.

BPA(OTf)$_2$ (4.62 g, 9.38 mmol), bis(pinacolato)diboron (5.24 g, 20.6 mmol, 2.2 equiv), potassium acetate (4.60 g, 46.9 mmol, 5 equiv), palladium acetate (42 mg, 0.19 mmol, 2%), and S-Phos (154 mg, 0.375 mmol, 4%) were combined in a 150 mL pressure vessel which was fitted with a septum and put under an argon atmosphere. Anhydrous toluene (30 mL) and argon-sparged H$_2$O (3 mL) were added to the vessel which was then sealed with the Teflon screw top. The reaction was stirred and heated to 90° C. overnight. After cooling, the reaction mixture was diluted with 50 mL of H$_2$O and 60 mL of CH$_2$Cl$_2$. The organic layer was separated and the aqueous layer was extracted with 2×30 mL CH$_2$Cl$_2$. The combined organics were washed with 75 mL of H$_2$O and 75 mL of brine. The solution was dried over MgSO$_4$, filtered, rotary evaporated, and then dried under dynamic vacuum to remove toluene. The solid residue was washed with hexanes to remove residual bis(pinacolato)diboron starting material. The final product was dried under dynamic vacuum overnight. Yield=3.35 g (80%) of a light-gray powder. TLC (4:1 hexane:EtOAc) shows a single spot with R$_f$=0.62 that stains blue in anisaldehyde indicating presence of the boronate ester group. $^1$H NMR (CDCl$_3$): 7.71 (d, Ar—H, 4H), 7.23 (d, Ar—H, 4H), 1.67 (s, ArC(CH$_3$)$_2$, 6H), 1.31 (s, pinacol ester, 12H). The NMR spectrum is shown in FIG. 24.

Example 2d: Synthesis of dimethyldiphenylmethane ethyl reverse-methacrylate (DMDPE-reverse-MA), according to Scheme 6.

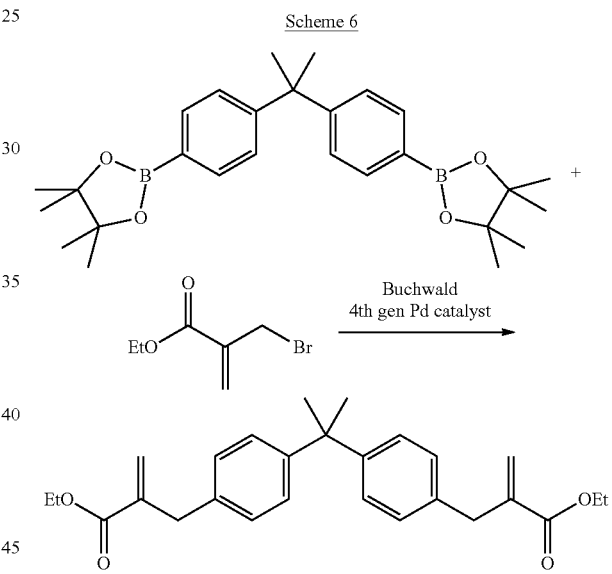

Scheme 6

Figure 25:
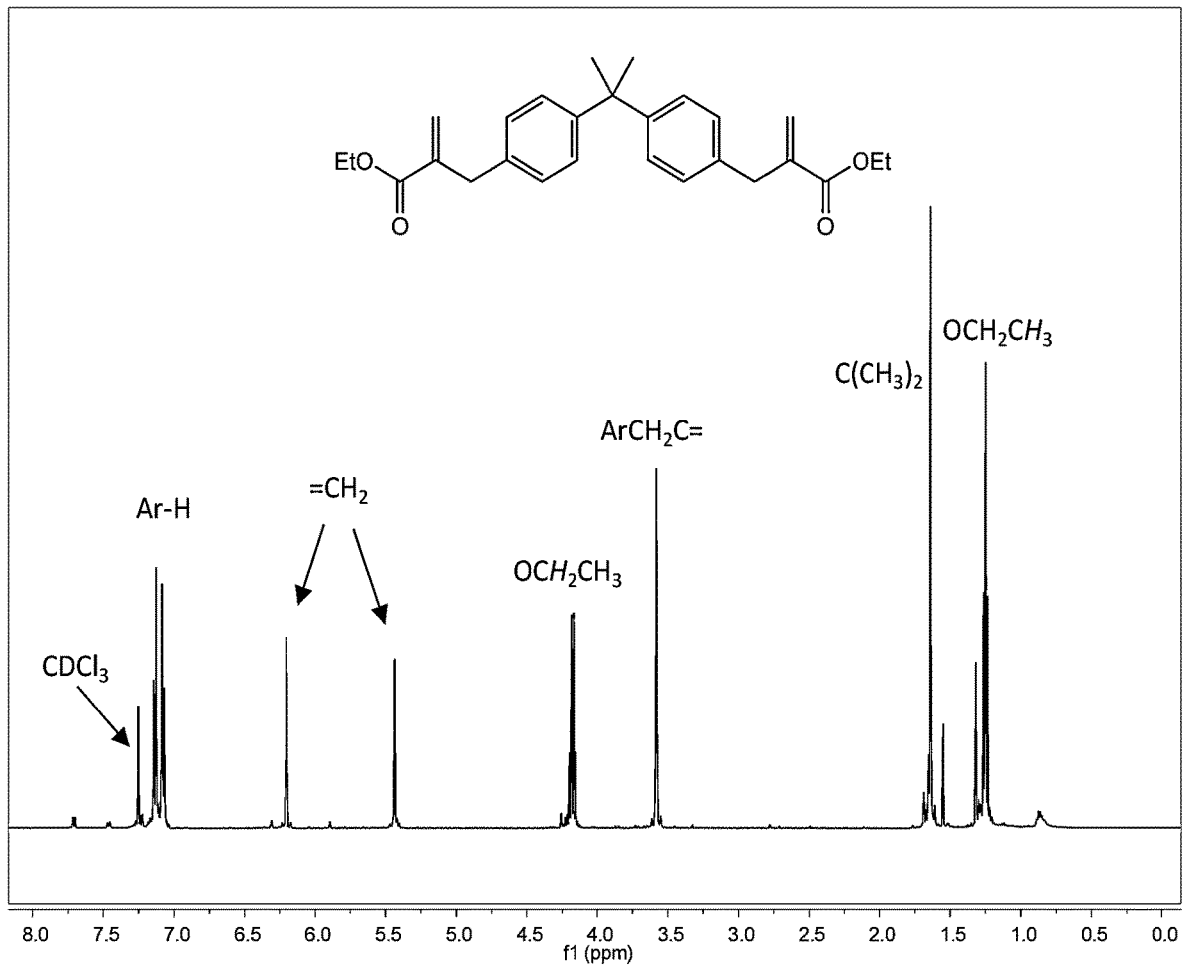
FIG. 25. The $^1$H-NMR spectrum of DMDPE-reverse-MA.

Dimethyldiphenylmethane(Bpin)$_2$ (2.00 g, 4.46 mmol), K$_3$PO$_4$ (2.85 g, 13.4 mmol), and Buchwald 4$^{th}$ gen XPhos Palladacycle catalyst (dicyclohexylphosphino-2',6'-dimethoxy-1,1'-biphenyl)(2'-methylamino-1,1'-biphenyl-2-yl) palladium(II), 80 mg, 93 µmol, 2%) were placed in a 150 mL round bottom flask under an argon atmosphere. Anhydrous THF (10 mL) and argon-sparged H$_2$O (8 mL) were added to the flask. Ethyl 2-bromomethylacrylate (1.30 mL, 9.43 mmol) was added via a syringe. The gray-tan heterogeneous reaction mixture was stirred at ambient temperature for 48 h. It was then diluted with 50 mL of water. It was extracted with 3×50 mL of CH$_2$Cl$_2$, and the combined organics were washed with 2×50 mL of H$_2$O and 75 mL of brine. The solution was dried over MgSO$_4$, filtered, and rotary evaporated to give a tacky white solid. TLC showed a combination of dimethyldiphenylmethane(Bpin)$_2$ and the desired product. The majority of the starting material was removed by extracting the crude product with hexane. It was then purified by flash chromatography on silica gel eluting with 12:1 hexanes:EtOAc; the crude is loaded as the yellow hexane extract. The pure fractions were subjected to rotary evaporation and the final product was dried under dynamic vacuum. Yield=0.89 g (47%) of a viscous, colorless liquid. TLC (4:1 hexane:EtOAc): $R_f$=0.55. $^1$H NMR (CDCl$_3$): 7.14 (d, Ar—H, 4H), 7.08 (d, Ar—H, 4H), 6.21 (s, =CH$_2$, 2H), 5.44 (s, =CH$_2$, 2H), 4.18 (q, OCH$_2$CH$_3$, 4H), 3.59 (s, Ar—CH$_2$, 4H), 1.65 (s, ArC(CH$_3$)$_2$, 6H), 1.24 (t, OCH$_2$CH$_3$, 6H). MS: m/z 420. The NMR spectrum is shown in FIG. 25.

Figure 26:
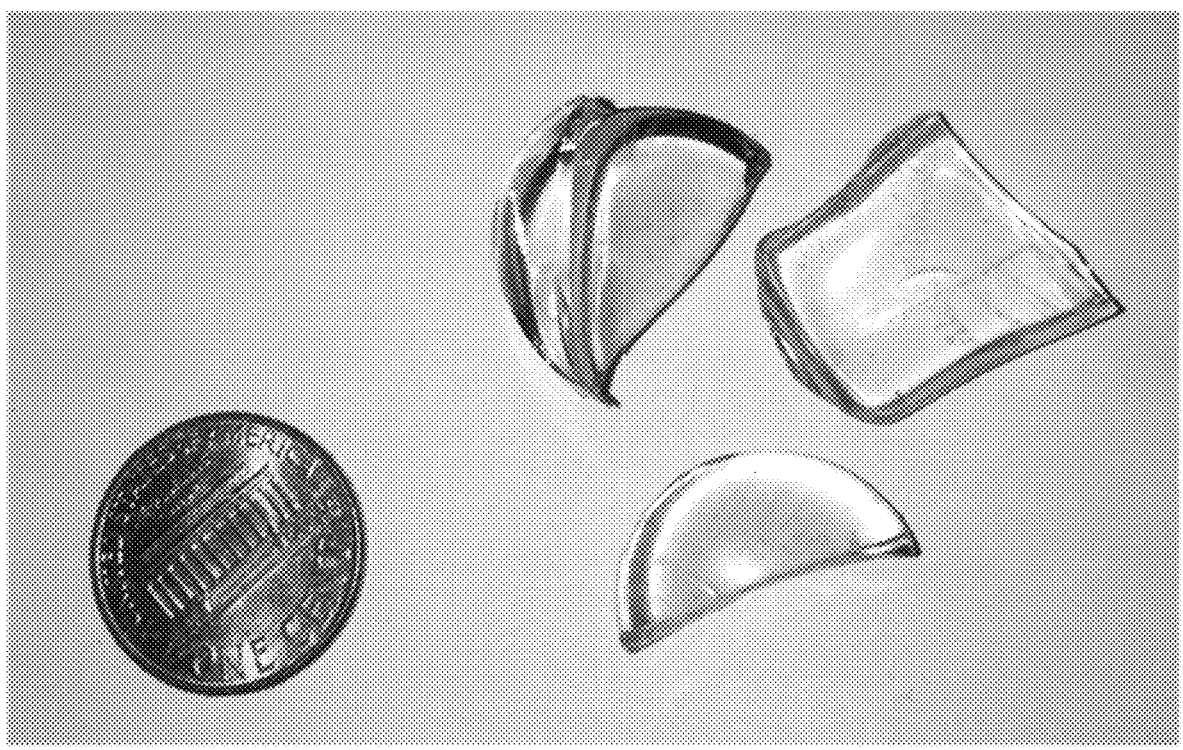
FIG. 26. A photograph of solid samples of polymerized EGE-reverse-MA, next to a one-cent coin for scale.
Figure 27:
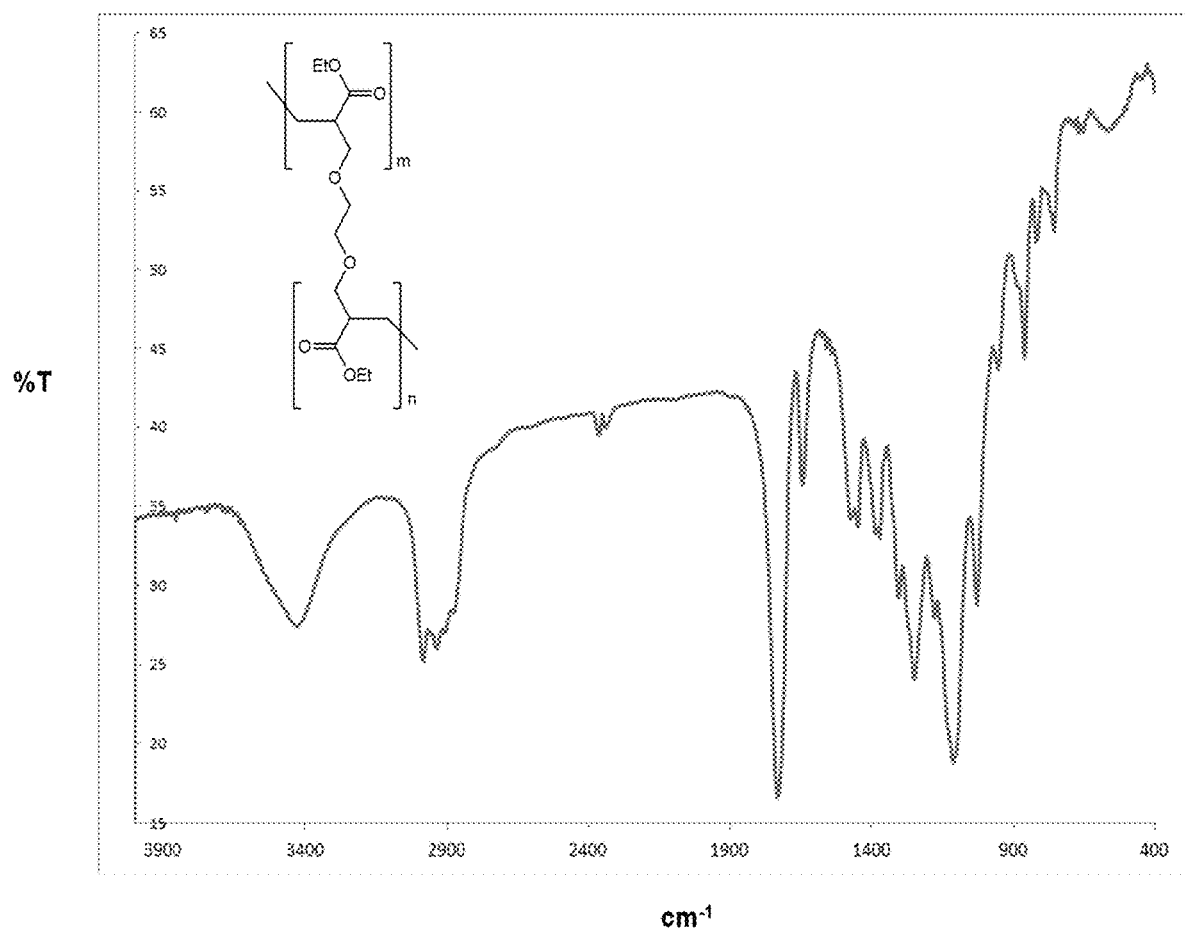
FIG. 27. The FTIR spectrum of polymerized EGE-reverse-MA (KBr pellet).

Example 3: characterization of monomers and preparation of crosslinked polymer networks. The above reaction sequences were used to generate 12 g of pure EGE-reverse-MA, and 6 g of DMDPE-reverse-MA. EGE-reverse-MA was found to be a liquid at room temperature, and remains a liquid at 0° C. The viscosity of EGE-reverse-MA is 10 cP at room temperature. EGE-reverse-MA can be stored with an added stabilizer to retard spontaneous polymerization. Trace amounts of MEHQ (4-methoxyphenol) can be added as a stabilizer to EGE-reverse-MA monomer samples for storage. The spontaneously formed EGE-reverse-MA crosslinked polymer network is clear and colorless. FIG. 26 shows samples of spontaneously polymerized EGE-reverse-MA polymer network and FIG. 27 shows the FTIR spectrum of this solid EGE-reverse-MA polymer. The ester C=O absorption at 1728 cm$^{-1}$ is prominent.

Polymerization (light-inducted curing) tests showed that the new monomers EGE-reverse-MA and DMDPE-reverse-MA have reaction properties that are comparable to the polymerization of EGDMA (ethylene glycol dimethacrylate, a typical conventional crosslinking acrylate monomer. Camphorquinone (CQ) was used as a visible light initiator, 2-hydroxy-2-methyl-propiophenone (HMPP) was used as an ultraviolet initiator, and diphenyliodonium hexafluorophosphate (Ph$_2$IPF$_6$) was used as a cationic initiator. The light sources for these tests were a Blak Ray 365 nm lamp (UV) and a Hilux dental curing lamp (visible blue light).

Samples of approximately 100 mg of EGDMA were treated with ca. 5 wt % of an initiator and mixed, and then a drop of the mixture was placed on a glass slide. The drop was then exposed to either UV or visible light for a period of a few minutes. The curing results for EGD-reverse-MA under different combinations of additives are shown in the upper portion of the table in FIG. 28. Next, the new ethylene glycol ethyl methacrylate (EGE-reverse-MA) monomer was tested in an identical manner. EGE-reverse-MA was found to cure in a similar manner to EGDMA, as summarized in the lower portion of the Table in FIG. 28. However, the EGE-reverse-MA does not lose mechanical properties as quickly as EGDMA under conditions that promote ester bond hydrolysis.

Although the present invention has been described in considerable detail with reference to certain preferred versions thereof, other versions are possible. Therefore, the spirit and scope of the appended claims should not be limited to the description of the preferred versions contained herein, except where required by 35 U.S.C.§ 112 ¶6 or 35 U.S.C.§ 112 (f).

The reader's attention is directed to all references which are filed concurrently with this specification and which are incorporated herein by reference.

All the features in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent of similar features. Any element in a claim that does not explicitly state "means for" performing a specified function, or "step for" performing a specific function, is not to be interpreted as a "means" or "step" clause as specified in 35 U.S.C.§ 112 ¶6 or 35 U.S.C.§ 112 (f). Any element in a claim that does explicitly state "means for" performing a specified function, or "step for" performing a specific function, is to be interpreted as a "means" or "step" clause as specified in 35 U.S.C.§ 112 ¶6 or 35 U.S.C.§ 112 (f).

What is claimed is:

1. A crosslink-forming monomer, comprising the chemical structure:

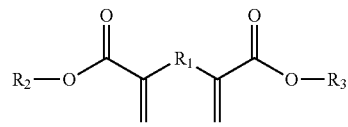

wherein, $R_1$ is selected from the group consisting of an alkyl, an aryl, an alkoxyl, and an alkylamino; wherein, $R_2$ is selected from the group consisting of an alkyl, an aryl, an alkoxyl, and an alkylamino; and $R_3$ is selected from the group consisting of an alkyl, an aryl, an alkoxyl, and an alkylamino.

2. The crosslink-forming monomer of claim 1, wherein $R_2$ is selected from the group consisting of a methyl, an ethyl, a propyl, an n-butyl and a t-butyl; and wherein, $R_3$ is selected from the group consisting of a methyl, an ethyl, a propyl, an n-butyl and a t-butyl.

3. The crosslink-forming monomer of claim 2, wherein $R_2$ and $R_3$ are each an ethyl group, the crosslink-forming monomer comprising the chemical structure:

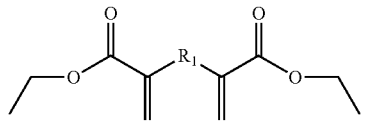

wherein, $R_1$ is selected from the group consisting of an alkyl, an aryl, an alkoxyl, and an alkylamino.

4. The crosslink-forming monomer of claim 3, further comprising the chemical structure:

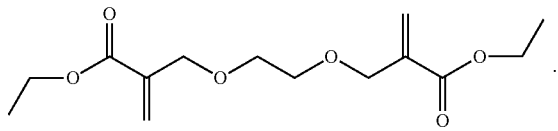 [SMILES: C=C(COCCOCC(=C)C(=O)OCC)C(=O)OCC]

5. The crosslink-forming monomer of claim 3, further comprising the chemical structure:

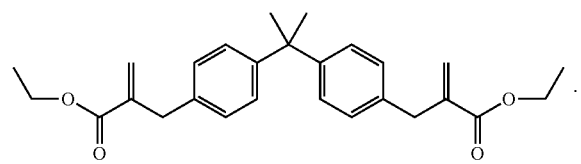 [SMILES: C=C(Cc1ccc(C(C)(C)c2ccc(CC(=C)C(=O)OCC)cc2)cc1)C(=O)OCC]

6. A crosslinked polymer network comprising crosslinks formed from the polymerization of the crosslink-forming monomer of claim 1, wherein the crosslinked polymer network comprises a plurality of crosslink group having the chemical structure:

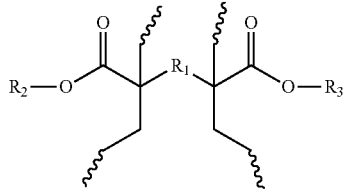

wherein, $R_1$ is selected from the group consisting of an alkyl, an aryl, an alkoxyl, and an alkylamino; wherein, $R_2$ is selected from the group consisting of an alkyl, an aryl, an alkoxyl, and an alkylamino; and $R_3$ is selected from the group consisting of an alkyl, an aryl, an alkoxyl, and an alkylamino.

7. The crosslinked polymer network of claim 6, wherein the crosslinked polymer network comprises a plurality of crosslink group having the chemical structure:

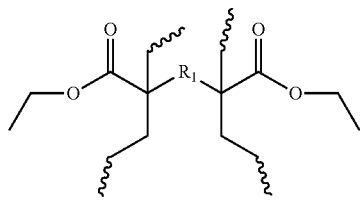

wherein, $R_1$ is selected from the group consisting of an alkyl, an aryl, an alkoxyl, and an alkylamino.

8. The crosslinked polymer network of claim 7, wherein the crosslinked polymer network comprises a plurality of crosslink group having the chemical structure:

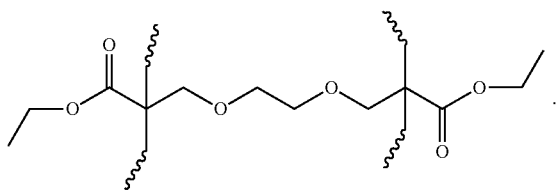

9. The crosslinked polymer network of claim 7, wherein the crosslinked polymer network comprises a plurality of crosslink group having the chemical structure:

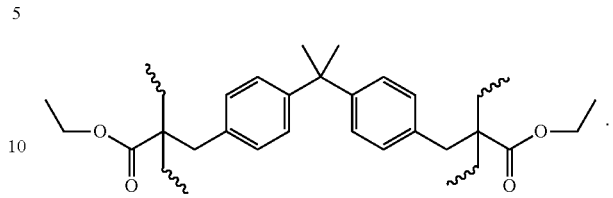

10. The crosslink-forming monomer of claim 1, further comprising the chemical structure:

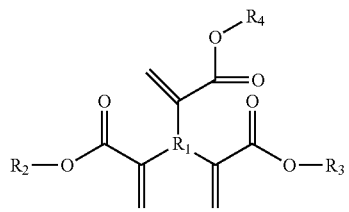

wherein, $R_1$ is selected from the group consisting of an alkyl, an aryl, an alkoxyl, and an alkylamino; wherein, $R_2$ is selected from the group consisting of an alkyl, an aryl, an alkoxyl, and an alkylamino; $R_3$ is selected from the group consisting of an alkyl, an aryl, an alkoxyl, and an alkylamino; and $R_4$ is selected from the group consisting of an alkyl, an aryl, an alkoxyl, and an alkylamino.

11. The crosslink-forming monomer of claim 10, wherein $R_2$ is selected from the group consisting of a methyl, an ethyl, a propyl, an n-butyl and a t-butyl; wherein, $R_3$ is selected from the group consisting of a methyl, an ethyl, a propyl, an n-butyl and a t-butyl; and wherein, $R_4$ is selected from the group consisting of a methyl, an ethyl, a propyl, an n-butyl and a t-butyl.

* * * * *